US008728518B2

(12) United States Patent
Liu et al.

(10) Patent No.: US 8,728,518 B2
(45) Date of Patent: May 20, 2014

(54) BUTYLPHTHALIDE SELF-EMULSIFYING DRUG DELIVERY SYSTEM, ITS PREPARATION AND METHOD AND APPLICATION

(75) Inventors: Zhentao Liu, Hebei Province (CN); Liying Yang, Hebei Province (CN); Hanyu Yang, Hebei Province (CN); Yuqing Gao, Hebei Province (CN); Dongmin Shen, Hebei Province (CN); Wenmin Guo, Heibei Province (CN); Xiaolong Feng, Heibei Province (CN); Jia Zheng, Heibei Province (CN)

(73) Assignee: CSPC ZhongQi Pharmaceutical Technology (Shijiazhuang) Co., Ltd, Shijiazhuang, Hebei (CN)

( * ) Notice: Subject to any disclaimer, the term of this patent is extended or adjusted under 35 U.S.C. 154(b) by 1694 days.

(21) Appl. No.: 11/574,313

(22) PCT Filed: Aug. 26, 2005

(86) PCT No.: PCT/CN2005/001332
§ 371 (c)(1),
(2), (4) Date: Sep. 28, 2007

(87) PCT Pub. No.: WO2006/021160
PCT Pub. Date: Mar. 2, 2006

(65) Prior Publication Data
US 2008/0319056 A1    Dec. 25, 2008

(30) Foreign Application Priority Data
Aug. 27, 2004  (CN) .......................... 2004 1 0075068

(51) Int. Cl.
*A61K 9/66*          (2006.01)
(52) U.S. Cl.
USPC ........... 424/455; 424/450; 424/451; 424/452; 424/464; 424/489; 514/470; 514/937
(58) Field of Classification Search
None
See application file for complete search history.

(56) References Cited

U.S. PATENT DOCUMENTS

| 6,596,306 B1 | 7/2003 | Ho et al. |
| 7,070,802 B1 * | 7/2006 | Bhalani et al. ................ 424/455 |
| 2002/0119198 A1 * | 8/2002 | Gao et al. ...................... 424/486 |

FOREIGN PATENT DOCUMENTS

| CN | 1100097 A | 3/1995 |
| CN | 1257706 A | 6/2000 |
| CN | 1339297 | 3/2002 |
| CN | 1394880 | 2/2003 |
| CN | 1478474 | 3/2004 |
| EP | 1 170 003 B1 | 4/2006 |
| JP | 2004210634 | 7/2004 |
| WO | WO 99/49848 A1 | 10/1999 |
| WO | WO 99/56727 A2 | 11/1999 |

OTHER PUBLICATIONS

Chang Q et al. Acta Pharmacol Sin Aug. 2003; 24(8) 796-804.*
BASF Cremophor (TM) RH40 Technical Information, Aug. 1997.*
Bachynsky, M.O., et al., "Factors Affecting the Efficiency of a Self-Emulsifying Oral Delivery System", *Drug Development and Industrial Pharmacy*, New York, NY, vol. 23, No. 8, Jan. 1, 2004, pp. 809-816.
Gursoy, R.N. et al., "Self-emulsifying drug delivery systems (SEDDS) for improved oral delivery of lipophilic drugs", *Biomedicine and Pharmacotherapy*, 200404 FR, vol. 58, No. 3, Apr. 2004, pp. 173-182.
International Search Report from related International Application No. PCT/CN2005/001332 mailed Nov. 3, 2005, 25 pages.

* cited by examiner

*Primary Examiner* — Hasan Ahmed
(74) *Attorney, Agent, or Firm* — Fish & Richardson P.C.

(57) ABSTRACT

The present invention relates to a novel drug delivery and release system, i.e. Self-emulsifying Drug Delivery System (SEDDS), of butylphthalide, to a preparation process thereof, and to a use thereof in a pharmaceutical formulation. The drug delivery system comprises as essential ingredients 1% to 65% of butylphthalide and 10% to 65% of a emulsifying agent, together with various excipients as required depending on the desired dosage forms. The present invention significantly increases the contact area between butylphthalide and the mucous membrane of the gastrointestinal tract, and therefore improves the absorptivity of the drug.

14 Claims, 2 Drawing Sheets

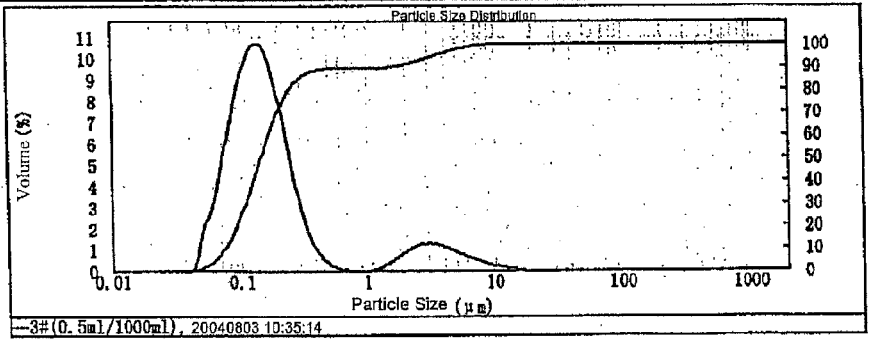
(to be continued)

| Particle Size (µm) | Volume Deficit% |
|---|---|
| 0.020 | 0.00 |
| 0.022 | 0.00 |
| 0.025 | 0.00 |
| 0.028 | 0.00 |
| 0.032 | 0.00 |
| 0.036 | 0.00 |
| 0.040 | 0.00 |
| 0.045 | 0.00 |
| 0.050 | 0.85 |
| 0.056 | 2.48 |
| 0.063 | 4.78 |
| 0.071 | 8.07 |
| 0.080 | 12.49 |
| 0.089 | 18.02 |
| 0.100 | 24.54 |
| 0.112 | 31.84 |
| 0.126 | 39.66 |

| Particle Size (µm) | Volume Deficit% |
|---|---|
| 0.142 | 47.69 |
| 0.159 | 55.59 |
| 0.178 | 63.01 |
| 0.200 | 69.65 |
| 0.224 | 75.25 |
| 0.252 | 79.73 |
| 0.283 | 83.06 |
| 0.317 | 85.41 |
| 0.356 | 86.99 |
| 0.399 | 87.94 |
| 0.448 | 88.53 |
| 0.502 | 88.87 |
| 0.564 | 89.04 |
| 0.632 | 89.11 |
| 0.710 | 89.11 |
| 0.796 | 89.11 |
| 0.893 | 89.11 |

| Particle Size (µm) | Volume Deficit% |
|---|---|
| 1.002 | 89.11 |
| 1.125 | 89.11 |
| 1.262 | 89.13 |
| 1.416 | 89.26 |
| 1.589 | 89.52 |
| 1.783 | 88.94 |
| 2.000 | 89.51 |
| 2.244 | 91.24 |
| 2.518 | 92.09 |
| 2.825 | 93.01 |
| 3.170 | 93.97 |
| 3.557 | 94.90 |
| 3.991 | 95.78 |
| 4.477 | 96.57 |
| 5.024 | 97.26 |
| 5.637 | 97.87 |
| 6.325 | 98.37 |

| Particle Size (µm) | Volume Deficit% |
|---|---|
| 7.096 | 98.79 |
| 7.962 | 99.13 |
| 8.934 | 99.40 |
| 10.024 | 99.61 |
| 11.247 | 99.77 |
| 12.619 | 99.88 |
| 14.159 | 99.95 |
| 15.887 | 100.00 |
| 17.825 | 100.00 |
| 20.000 | 100.00 |
| 22.440 | 100.00 |
| 25.179 | 100.00 |
| 28.251 | 100.00 |
| 31.698 | 100.00 |
| 35.566 | 100.00 |
| 39.905 | 100.00 |
| 44.774 | 100.00 |

| Particle Size (µm) | Volume Deficit% |
|---|---|
| 50.238 | 100.00 |
| 56.368 | 100.00 |
| 63.246 | 100.00 |
| 70.963 | 100.00 |
| 79.621 | 100.00 |
| 89.337 | 100.00 |
| 100.237 | 100.00 |
| 112.468 | 100.00 |
| 126.191 | 100.00 |
| 141.589 | 100.00 |
| 158.866 | 100.00 |
| 178.250 | 100.00 |
| 200.000 | 100.00 |
| 224.404 | 100.00 |
| 251.785 | 100.00 |
| 282.508 | 100.00 |
| 316.979 | 100.00 |

| Particle Size (µm) | Volume Deficit% |
|---|---|
| 355.656 | 100.00 |
| 399.052 | 100.00 |
| 447.744 | 100.00 |
| 502.377 | 100.00 |
| 563.677 | 100.00 |
| 632.456 | 100.00 |
| 709.627 | 100.00 |
| 796.214 | 100.00 |
| 893.367 | 100.00 |
| 1002.374 | 100.00 |
| 1124.683 | 100.00 |
| 1261.915 | 100.00 |
| 1415.892 | 100.00 |
| 1588.656 | 100.00 |
| 1782.502 | 100.00 |
| 2000.000 | 100.00 |

Continued

BUTYLPHTHALIDE SELF-EMULSIFYING DRUG DELIVERY SYSTEM, ITS PREPARATION AND METHOD AND APPLICATION

FIELD OF THE INVENTION

The present invention relates to a novel drug delivery and release system of butylphthalide, and particularly relates to butylphthalide self-emulsifying drug delivery system, and its preparation process and use in pharmaceutical formulations.

BACKGROUND OF THE INVENTION

Self-Emulsifying Drug Delivery System (SEDDS) is a solid or liquid dosage form comprising an oil phase, a surfactant and a cosurfactant, characterized primarily in that said dosage form can form oil-in-water emulsion spontaneously in the gastrointestinal tract or at ambient temperature (referring generally to body temperature, namely 37° C.) with mild stirring. As the amount of the emulsifying agent increases, such a self-emulsifying system can form micro-emulsion in the gastrointestinal tract spontaneously, and thus is called Self-microemulsifying Drug Delivery System (SMEDDS). When SEDDS enters the gastrointestinal tract, it is firstly self-emulsified as emulsion droplets and rapidly dispersed throughout the gastrointestinal tract, and thus reducing the irritation caused by the direct contact of the drug with the mucous membrane of the gastrointestinal tract. In the gastrointestinal tract, the structure of the emulsion microparticulates will be changed or destroyed. The thus-formed microparticulates of micrometer or nanometer level can penetrate into the mucous membrane of the gastrointestinal tract, and the digested oil droplets enter the blood circulation, thereby significantly improving the bioavailability of the drug. The self-emulsifying drug delivery system is predominantly employed with respect to lipid-soluble and less water-soluble drugs. It can increase the stability and the bioavailability of the drugs.

Butylphthalide is a primary component in celeries and seeds thereof. It can be obtained by direct extraction from natural celery seed oil, or by synthesis. Chinese Patent for Invention No. 98125618.X disclosed the use of L-n-butylphthalide in the manufacture of an anti-thrombotic and anti-platelet agglutination drug, clearly demonstrating that L-n-butylphthalide can regulate the function of the NOS-NO-cGMP system and the metabolism of arachidonic acid in neuronal cells after cerebral ischemia. Chinese Patent for Invention No. 93117148.2 disclosed the use of butylphthalide in the manufacture of a medicament for preventing and treating a disorder caused by cerebral ischemia in a mammal or a human, wherein said butylphthalide is a liquid oil with no optical activity. It has an intense flavor of celery, and has the following formula:

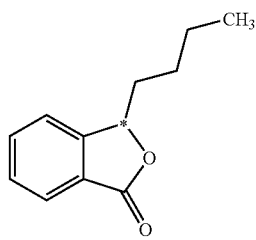

Currently, butylphthalide is commercially available only in the form of soft capsule, that is, butylphthalide is dispersed in vegetable oil and then directly filled into soft capsules. Though such a dosage form can mask the unpleasant odor of the agent, yet its content is poorly dispersed in an aqueous phase, and the extent of its dissolution in vitro cannot be directly determined, which not only obstructs the quality control during the production of the product, but also affects the absorption rate of the drug to a great extent.

In addition, in Chinese Patent for Invention No. 02123000.5, the present inventors disclosed a technique to improve the water solubility of butylphthalide through the inclusion of cyclodextrin derivative. This technique not only masked the unpleasant odor but also increased the water solubility of butylphthalide. However, the amount of the primary component being used during the preparation of the inclusion substances is limited by the volume of the dosage form, and thus various dosage forms cannot be supplied to meet the requirements of patients. For example, the preparation of hard capsule dosage is limited by the loading capability, the preparation of tablets is limited by the suitability of tablet size, and the amount of the primary component in the inclusion substances cannot be too large. Furthermore, the inclusion process consumes more power, has more processing steps, is more complex to be operated, and requires more process control points (such as the temperature, grinding mode and strength, time, stirring rate and duration). So the industrialization of said product inclusion technique is relatively slow.

SUMMARY OF THE INVENTION

An object of the present invention is to overcome the disadvantage of the above butylphthalide preparations in clinical use, and to provide a novel drug delivery system for butylphthalide, i.e. a self-emulsifying drug delivery system of butylphthalide.

The self-emulsifying drug delivery system of butylphthalide provided in the present invention comprises as essential components 1% to 65 wt % of butylphthalide, 10% to 65 wt % of an emulsifying agent, and preferably comprises as essential components 10 wt % to 50 wt % of butylphthalide, 15 wt % to 60 wt % of an emulsifying agent, together with various excipients appropriately depending on the desired dosage forms to produce corresponding dosage forms, wherein the appropriate amount of the excipients used is 0 to 85%, preferably 5 to 75% (each of the above amounts is based on the total weight of the self-emulsifying drug delivery system for butylphthalide).

Butylphthalide is selected from the group consisting of its racemic, levo-rotary and dextro-rotary isoforms.

The self-emulsifying drug delivery system of the present invention is also useful for the delivery of oil-soluble derivatives of butylphthalide.

In the present invention, preferably SEDDS emulsifying agents are non-ionic emulsifying agents. Non-ionic emulsifying agents are less toxic than ionic emulsifying agents, and merely induce reversible changes to the permeability of the mucous membrane of the gastrointestinal tract. SEDDS emulsifying agents of the present invention are selected from any of the group consisting of liquid or solid ethoxy polyoxyethylene glyceride, polyoxyethylene oleoate, liquid lecithin (e.g. OPHASE 31™, HLB=4.0), polyoxyethylene castor oil (CREMOPHOR EL™, HLB=13.5), coconut oil, polyethyleneglycol glyceride( LABRAFAC CM10™, HLB=10), almond oil oleic acid polyethyleneglycol glyceride (LABRAFIL M1944CSD ™, HLB=3 to 4; LABRAFIL M2125CS ™, HLB=3 to 4), polyoxyethylene (25) glycerin trioleoate TAGAT TO ™, HLB=11.3), polyoxyethylene (20) sorbitan oleoate TWEEN 80 ™, HLB=11.0), polyethyleneglycol-8 glycerin caprylate/caprate LABRASOL ™, HLB=14) and the like, or the mixture of any two or more thereof.

Preparation Procedure: The emulsifying agents are completely melted in water bath at 20 to 60° C. and mixed, then butylphthalide is added with agitation, and excipients are added, to produce a dosage form of the butylphthalide self-emulsifying drug delivery system.

The present invention also provides a series of formulations of butylphthalide self-emulsifying drug delivery, and various butylphthalide dosage forms with a mechanism of self-emulsifying drug delivery, together with excipients appropriate for corresponding dosage forms, such as tablets, soft capsules, granules, hard capsules and oral liquids for self-emulsifying drug delivery of butylphthalide.

The self-emulsifying drug delivery system for butylphthalide of the present invention is especially useful for a dosage form of soft capsule, whose content is a liquid oil of a self-emulsifying feature, which comprises butylphthalide, an emulsifying agent, and optionally an excipient. The excipients are selected from any one of the group consisting of edible plant oils, for example sesame oil, corn oil, peanut oil, soybean oil, almond oil, peach kernel oil, cotton seed oil, sunflower seed oil, and oliver oil, or the mixture of any two or more thereof. Optionally, the dosage form may additionally comprise an anti-oxidant and a lipophilic flavoring.

The excipients contained in the self-emulsifying soft capsules of the present invention can be conventional excipients in the art. The butylphthalide self-emulsifying drug delivery system of the present invention can also be useful for a dosage form of oral liquid, which is a liquid oil of a self-emulsifying feature and can be administered after being diluted with water. Into the above-mentioned butylphthalide self-emulsifying drug delivery system, water, solubilizing agents, and appropriate flavorings can also be added to directly obtain an oral liquid.

The butylphthalide self-emulsifying drug delivery system of the present invention may also be useful in the form of oral solid powders or granules. The oral solid formulations of the butylphthalide self-emulsifying drug delivery system of the present invention, such as tablets (including delayed capsules, and controlled release tablets), capsules (including delayed, and controlled release capsules), granules and the like, can be obtained by incorporating excipients as required by the oral solid formulations, such as disintegrants, binders, flavorings, and/or polymeric scaffold materials, etc., to the aforementioned butylphthalide self-emulsifying drug delivery system, resulting in solid powders or granules of a self-emulsifying feature by conventional techniques.

Tablets of the butylphthalide self-emulsifying drug delivery system according to the present invention can be produced by mixing solid powders or granules being capable of self-emulsification with appropriate plasticizing agents, disintegrants and lubricants, and subsequently pressing with appropriate mould size. If necessary, the tablets can be coated with an appropriate coating such as a gastric coating, enteric coating, or delayed or controlled drug release coating including cellulose acetate, ethyl cellulose and the like.

Hard capsules of the butylphthalide self-emulsifying drug delivery system according to the present invention can be produced by combining solid powders or granulesbeing capable of self-emulsification with conventional lubricants, delayed release materials and the like, resulting in normal hard capsules, or controlled or delayed release capsules.

The content in the self-emulsifying soft capsules of the present invention is an oil liquid capable of self-emulsification. When the capsules are disintegrated in water, the drug is rapidly dispersed into water to form an oil-in water emulsion. As a result, product quality can be assessed by the dissolution test. Additionally, the contact area of butylphthalide with the gastrointestinal tract is greatly increased, thereby increasing the absorption rate of the drug. The self-emulsifying drug delivery system of the present invention can be prepared by a single and easily operated process. Moreover, it has the advantages of lower power consumption during its production or preparation process and a high degree of industrialization, etc.

Butylphthalide self-emulsification soft capsules have the properties of its strong special odor being masked by the normal soft capsules, administration convenience, easy swallowing, and good compliance of patients. Moreover, they allow the oily active ingredients to be rapidly dispersed when getting contact with the gastric fluid to form an oil-in-water emulsion, thereby increasing the extent and the rate of absorption. The present formulation is shown in the acceleration test and the long-term test that, although the aging of the shell of the present soft capsule is significant when being heated and the disintegration time is elongated, it is still less than 60 minutes, and thus complies with the provisions of Chinese Pharmacopoeia. Various parameters such as appearance, content, degradation products, the time for self-emulsification and the in vitro release degree of the present formulation are not significantly changed.

BRIEF DESCRIPTION OF THE DRAWINGS

FIG. 1 shows the result of the particle size distribution of butylphthalide self-emulsification system being measured with a laser particle size distribution analyzer. From FIG. 1, it can be seen that more than 98% of the emulsion droplets have a particle size of less than 5 μm, and thus said system belong to a self-microemulsifying drug delivery system. It can also be concluded from the volume less-than-percentage profile in FIG. 1 that particle size distribution in the present system is narrow and uniform.

DETAILED DESCRIPTION OF THE INVENTION

A soft capsule is used in the present invention as a preferred dosage form of the butylphthalide self-emulsifying drug delivery system.

The content in the soft capsule of the self-emulsifying drug delivery of the present invention comprises butylphthalide and an emulsifying agent, preferably in the following percentages by weights: 10% to 50% of butylphthalide, and 15% to 60% of said emulsifying agent. Into the oily liquid of the drug can also be added an appropriate antioxidant such as dibutyl hydroxytoluene and a flavoring agent such as mint oil, green apple oil, and the like.

The emulsifying agent is preferably the mixture of polyoxyethylene castor oil and polyethyleneglycol-8 glycerin caprylate/caprate preferably in the ratio of 1:0.5 to 1.5 (by weight). The ratio of butylphthalide to the emulsifying agent is preferably 1:0.5 to 1.5 (by weight).

Preferred Preparation Process: Hydrogenated castor oil is adequately melted in a water bath at 25 to 50° C., then polyethyleneglycol-8 glycerin caprylate/caprate is added and mixed with agitation to obtain a homogenous clear oily liquid. Butylphthalide is added and mixed with agitation at room temperature. The contents for the soft capsules are thus obtained.

The shell of the soft capsule of the self-emulsifying drug delivery system according to the present invention consists essentially of shell composition, plasticizing agent, and water in the ratio by weight of 1:0.2 to 0.4:0.8 to 1.3. Furthermore, into the shell can also be incorporated appropriate preservative such as ethylparaben, methylparaben or a mixture thereof.

The shell composition can be gelatin, acacia gum, or a mixture thereof.

The plasticizing agent can be glycerin, sorbitol, or a mixture thereof.

The present butylphthalide soft capsule can be produced by conventional processes for the preparation of soft capsules, such as the manual compression moulding method, the rotary compression moulding method or the dropping method. Generally, the compression methods such as the rotary compression moulding method is employed, using an automatic rotary capsule-rolling machine, with the temperature being controlled in the range of 40 to 50° C., so that each soft capsule contains a pharmaceutically acceptable amount of butylphthalide.

The following examples are shown to describe the embodiments of the present invention in detail. They are not intended to limit the scope of the present invention.

EXAMPLE 1

Preparation of Butylphthalide Self-emulsification Soft Capsules

Preparation of Gelatin Solution: 100 g of gelatin, 30 g of glycerin, 130 g of water and 200 mg of ethylparaben are used. An appropriate amount of water is added into gelatin, allowing it to absorb water and to swell. Glycerin, ethylparaben and residual water are placed into a tank and heated to a temperature of 70 to 80° C., and homogeneously mixed. Swollen gelatin is added with agitation, melted, incubated for 1 to 2 hrs, and kept rest for foams to float up. The floating foams are then scraped, and the remainder is filtered through a clean white cloth and kept warm for further use. The viscosity of the resulting gum liquid is generally 2.8 to 3.2 degree.

Preparation of oily liquid of butylphthalide: 100 g of butylphthalide, 50 g each of polyethyleneglycol-8 glycerin caprylate/caprate and polyoxyethylene castor oil are weighed and thoroughly agitated to obtain the oily liquid.

Compression of soft capsules: the prepared gelatin glycerin and oily liquid of butylphthalide are placed into an automatic rotary capsule-rolling machine, and the temperature is kept at 40 to 50° C. Soft capsules each containing 200 mg of the oily liquid are encapsuled.

The soft capsules have an appropriate size in appearance and good content consistency as measured.

EXAMPLE 2

Validation of the Process for Preparing Butylphthalide Self-Emulsification Soft Capsules Preparation of the Gelatin Solution: 1000 g of gelatin, 300 g of glycerin, 1300 g of water and 2000 mg of ethylparaben are used. An appropriate amount of water is added into the gelatin, allowing it to absorb water and swell. Glycerin, ethylparaben and residual water are placed into a tank and heated to a temperature of 70 to 80° C., and homogeneously mixed. The swollen gelatin is added with agitation, melted, incubated for 1 to 2 hrs, and kept rest for foams to float up. The floating foams are then scraped, the remainder is filtered through a clean white cloth and kept warm for further use. The viscosity of the resulting gum liquid is generally 2.8 to 3.2 degree.

Preparation of oily liquid of butylphthalide: 1000 g of butylphthalide, 500 g each of polyethyleneglycol-8 glycerin caprylate/caprate and polyoxyethylene castor oil are weighed and thoroughly mixed to get the oily liquid.

Compression of soft capsules: The thus prepared gelatin glycerin and the oily liquid of butylphthalide are placed into an automatic rotary capsule-rolling machine, and the temperature is kept at 40 to 50° C. Soft capsules each containing 200 mg of the oily liquid are encapsuled.

The resulting soft capsules prepared at the above ratios have an appropriate size in appearance and good content consistency as measured.

Three batches of samples are prepared according to the procedure in Example 2. The consistencies of the dissolution and particle size are investigated for the three batches of the samples. The degree of dissolution and the particle size is determined as follows:

Dissolution Test: The present soft capsules are tested according to the Dissolution Test (Appendix X C: Method 2, in Chinese Pharmacopoeia, 2005 edition, Part II), where 900 ml of water is used as the solvent, and the rotatory rate is set at 100 rpm. The test is performed as described. After 45 minutes, 10 ml of the solution is removed and filtered. 5 ml of the filtrate is precisely removed and transferred into a 10 ml measuring flask. Methanol is added into the flask to the scale for dilution and homogeneously shaken. The absorbance at the wavelength of 280 nm is spectrophotometrically determined (Appendix IV A, in Chinese Pharmacopoeia, 2000 edition, Part II). 25.0 mg of the control sample of butylphthalide is precisely weighed and placed into a 50 ml measuring flask, methanol is added for dissolution and dilution to the scale, then mixed homogeneously. 5 ml of the solution is precisely taken and placed into a 50 ml measuring flask, then 20 ml of methanol is added. Water is supplemented into the flask to the scale for dilution, and homogeneously shaken. The resultant solution is used as the control and measured by the same procedure. The dissolution of each capsule is calculated and the results are shown in Table 1.

Analysis of the Particle Size Distribution:

Model Nano-ZS of MALVERN Particle Size Analyzer is used. Protocol: the content of the present capsules is taken and diluted by 100 times with artificial gastric fluid and used as the test solution. 1 ml of aliquot is placed into a sample cell. The measurement is performed at a setting temperature of 25° C. The range of the particle size distribution and summed distribution is analyzed using unimodality statistics. The results are shown in Table 2 and FIG. 1.

Microscopic analysis: 0.2 ml of the oily liquid is aliquoted and dropwise added into 100 ml of the artificial gastric fluid at 37° C. with mild agitation, and immediately a homogeneous oil-in-water emulsion is formed spontaneously. 10 µl of the thus-formed emulsion is placed on a glass slide for microscopic investigation.

Statistically 98.7% of the emulsion droplets have a particle size of smaller than 5 µm, which is substantially consistent with the results as measured by MALVERN particle size distribution analysis, and lies within the range of microemulsification. So it is designated as butylphthalide self-emulsifying (self-microemulsifying) drug delivery system based on the characteristics of the present dosage form.

TABLE 1

Results of three batches of the samples in the dissolution test

| item | Dissolution % 031201 | 031202 | 031203 | Remark |
|---|---|---|---|---|
| Self-emulsification (45 min) | 100.01 | 99.6 | 98.9 | When being disintegrated, the content forms a homogeneous emulsion spontaneously if getting contact with water. Samples can be directly taken for measurement. |
| Normal soft capsule (60 min) | 95.4 | 96.8 | 92.5 | When being disintegrated, oil drops adhere to the wall of the flask or float on the surface without dispersion. The analysis can be performed only when an emulsifying agent is added into the dissolution medium. |
| Conclusion 2 | | | | The self-emulsifying formulation is dissolved more uniformly and the quality can be controlled. |

TABLE 2

Particle size distribution measured for 3 batches of the samples

| Particle Size | Particle Size Distribution % 031201 | 031202 | 031203 | Remark |
|---|---|---|---|---|
| >5 μm | 2.78 | 3.05 | 2.54 | Totally 300 particulates per batch are counted. |
| 1 to 5 μm | 4.64 | 5.64 | 5.01 | |
| <1 μm | 92.68 | 91.31 | 92.45 | |
| Conclusion 1 | | | | All of the three batches of the samples are self-emulsifying drug delivery systems. |

The experimental data on stability of the present soft capsules are shown in Table 3:

TABLE 3

Preliminary stability test of the butylphthalide self-emulsification soft capsules

| Condition | Time (month) | Appearance | Content (wt %) | Degrd. Product (wt %) | Time for self-emulsification (sec.) | In vitro release (wt %) | Time for disintegration |
|---|---|---|---|---|---|---|---|
| Start | 0 | Yellow clear soft capsule | 100.3 | 0.61 | 2.33 | 99.3 | 5'50" |
| Acceleration Test | 1 | Yellow clear soft capsule | 101.1 | 0.66 | 2.67 | 100.2 | 6'45" |
| | 2 | Yellow clear soft capsule | 99.3 | 0.63 | 3.33 | 99.6 | 14'10" |
| | 3 | Yellow clear soft capsule | 98.4 | 0.62 | 3.5 | 100.2 | 28'30" |
| | 6 | Yellow clear soft capsule | 99.0 | 0.58 | 3.33 | 98.5 | 49'52" |
| Room temp. | 1 | Yellow clear soft capsule | 100.1 | 0.63 | 2.50 | 100.5 | 6'15" |
| | 3 | Yellow clear soft capsule | 101.0 | 0.67 | 2.50 | 98.9 | 8'35" |
| | 6 | Yellow clear soft capsule | 99.4 | 0.66 | 2.67 | 100.1 | 9'45" |
| | 12 | Yellow clear soft capsule | 99.1 | 0.62 | 2.83 | 99.7 | 17'50" |

EXAMPLE 3

Preparation of Soft Capsules of Butylphthalide 100 g of butylphthalide, 50 g each of polyethyleneglycol-8 glycerin caprylate/caprate and polyoxyethylene castor oil are weighed, the subsequent steps are the same as in Example 1, except that in the preparation of the oily liquid, a solubilizing agent such as 20 g of propylene glycol is additionally incorporated and thoroughly mixed. Each of the final soft capsules contains 220 mg of the oily liquid of butylphthalide.

EXAMPLE 4

Preparation of Soft Capsules of Butylphthalide

Preparation of Gelatin Solution: 100 g of gelatin, 40 g of glycerin, 120 g of water and 200 mg of ethylparaben are used. The gelatin solution is prepared by the same protocol as in Example 1.

Preparation of the oily liquid of butylphthalide: 500 g of butylphthalide, 600 g of polyethyleneglycol-8 glycerin caprylate and 500 mg of orange flavoring agent are weighed and thoroughly mixed to obtain the oily liquid.

Compression of soft capsules: The procedure is the same as in Example 1, except that each of the final compressed soft capsules contains 220 mg of the oily liquid of butylphthalide.

EXAMPLE 5

Preparation of Soft Capsules of Butylphthalide

Preparation of oily liquid of butylphthalide: 100 g of butylphthalide, 65 g of polyethyleneglycol-8 glycerin caprylate/caprate, and 50 g of polyoxyethylene castor oil are weighed and homogeneously mixed, resulting in a clear oily liquid.

Preparation of Gelatin Solution: 100 g of gelatin, 30 g of glycerin, 120 g of water and 20 g of PEG400 are used. The protocol for preparing the gelatin solution is the same as in Example 1.

The steps are the same as in Example 1, except that each of the final soft capsules contains 210 mg of the oily liquid of butylphthalide.

EXAMPLE 6

Preparation of Soft Capsules of Butylphthalide 100 g of butylphthalide, 40 g of polyethyleneglycol-8 glycerin caprylate/caprate, and 50 g of polyoxyethylene castor oil are weighed and thoroughly mixed to obtain a clear oily liquid.

Preparation of Gelatin Solution: 100 g of gelatin, 40 g of glycerin, 120 g of water and 10 g of PEG400 are used. The procedure for preparing the gelatin solution is the same as in Example 1.

The other steps are performed in the same way as in Example 1, except that each of the final soft capsules contains 190 mg of the oily liquid of butylphthalide.

EXAMPLE 7

Preparation of Self-emulsifying Granules of Butylphthalide 100 g of butylphthalide, 100 g of polyethyleneglycol-8 glycerin caprylate, 20 g of ethanol, 100 mg of mint oil and 100 mg of orange flavoring are mixed together to be used as a binder, then being added to the mixture of 450 g of sugar powder and 5 g of low substituted cellulose (L-HPC). The resultant mixture is granulated and dried.

EXAMPLE 8

Preparation of Self-emulsifying Granules of Butylphthalide 100 g of butylphthalide, 50 g of polyethyleneglycol-8 glycerin caprylate, 50 g of hydrogenated castor oil, 100 mg of mint oil and 100 mg of green apple flavoring are mixed together to be used as a binder, then being added to the mixture of 400 g of sugar powder, 100 g of PVP and 5 g of low substituted cellulose (L-HPC). The resultant mixture is granulated through mesh #20, dried, and distributed into packages.

EXAMPLE 9

Preparation of Self-emulsifying Tablets of Butylphthalide 100 g of butylphthalide, 50 g of polyethyleneglycol-8 glycerin caprylate, and 40 g of hydrogenated castor oil are mixed together to be used as a binder, then being added to the mixture of 100 g of sugar powder, 40 g of sodium carboxymethyl starch, and 150 g of microcrystalline cellulose. The resultant mixture is granulated through mesh #32, and dried at 45° C. Then additionally 5 g of magnesium stearate as a lubricant and green apple solid powder essence as a flavoring are added and mixed. Then tablets are formed by compression, each with a weight of about 0.49 g.

EXAMPLE 10

Preparation of Self-emulsifying Tablets of Butylphthalide

Tablet core: 100 g of butylphthalide and 50 g of polyethyleneglycol-8 glycerin caprylate are mixed together as a binder, then being added into the mixture of 100 g of sugar powder, 40 g of sodium carboxymethyl starch, and 150 g of microcrystalline cellulose. The resultant mixture is granulated through mesh #32, and dried at 45° C. Additionally 5 g of magnesium stearate is added as a lubricant and mixed. Then tablets are formed by compression, each with a weight of about 0.49 g.

Coating: 60 g of hydroxypropyl methyl cellulose is dissolved in 1000 ml of 80% ethanol solution. 0.5 g of edible green coloring is added and mixed. The coating is performed by a rolling coating process, with the tablet bed temperature being at 35 to 45° C., resulting in light green film-coated tablets.

EXAMPLE 11

Preparation of Delayed Release Self-emulsifying Tablets of Butylphthalide 100 g of butylphthalide, 50 g of polyethyleneglycol-8 glycerin caprylate, 50 g of hydrogenated castor oil, and 100 mg of mint oil are mixed together as a binder, then being slowly added into the mixture of 100 g of hydroxypropyl methyl cellulose (HPMC$_{K100M}$), 80 g of hydroxypropyl methyl cellulose (HPMC$_{K4M}$), and 10 g of ethylcellulose. The resultant mixture is agitated homogeneously, granulated through mesh #32, dried at 45° C., and then sized through mesh #20.5 g of magnesium stearate as a lubricant is added and then tablets are pressed.

EXAMPLE 12

Preparation of Controlled Release Self-emulsifying Tablets of Butylphthalide

Tablet core: 100 g of butylphthalide and 50 g of polyethyleneglycol-8 glycerin caprylate are mixed together, then added to the powder mixture of 120 g of starch, 180 g of microcrystalline cellulose, 100 g of lactose, and 20 g of Poloxamer-188. The resultant mixture is agitated homogeneously, granulated through mesh #32, dried at 45° C., and sized through mesh #20.5 g of magnesium stearate as a lubricant is added. And then tablets are pressed and coated with 0.1 to 0.3 mm of hydroxypropyl cellulose-polyethylene acetate composite film.

EXAMPLE 13

Preparation of Butylphthalide Self-emulsifying Hard Capsules 50 g of butylphthalide and 20 g of polyethyleneglycol-8 glycerin caprylate are mixed together. Then 100 g of starch as an absorbing and diluting agent, 10 g of polyethylene pyrrolidone (PVP) as a binder, and 10 g of low substituted cellulose (L-HPC) as a disintegrant are added. The resultant mixture is granulated through mesh #32, dried at 45° C., and sized through mesh #20. Then magnesium stearate is added as a lubricant, and the granules are distributed into capsule shells #1.

EXAMPLE 14

Preparation of Butylphthalide Self-emulsifying Hard Capsules 50 g of butylphthalide and 20 g of polyethyleneglycol-8 glycerin caprylate are absorbed to 40 g of Poloxamer, 60 g of maltodextrin, 60 g of microcrystalline cellulose and 8 g of sodium carboxymethyl starch. The resultant mixture is granulated through mesh #32, dried at 45 to 50° C., and sized through mesh #20. After the addition of talc as a lubricant and mixing, the granules are distributed into capsule shells #2.

EXAMPLE 15

Preparation of Delayed Release Capsules of Self-emulsifying Butylphthalide 100 g of butylphthalide, 50 g of polyethyleneglycol-8 glycerin caprylate, 50 g of hydrogenated castor oil, 100 mg of mint oil, and 100 mg of green apple oil are mixed together as a binder, then slowly added to the mixture of 100 g of hydroxypropyl methyl cellulose (HPMC$_{K100M}$), 80 g of hydroxypropyl methyl cellulose (HPMC$_{K4M}$), and 10 g of ethylcellulose. The resultant mixture is agitated homogeneously, granulated through mesh #32, dried at 45° C., and then sized through mesh #20. After adding 5 g of magnesium stearate as a lubricant and mixing, the granules are distributed into capsule shells #1.

EXAMPLE 16

Preparation of Oral Liquid (Oil) of Self-emulsifying Butylphthalide 100 g of butylphthalide, 50 g of polyethyleneglycol-8 glycerin caprylate, 50 g of hydrogenated castor oil, 0.1 g of orange flavoring, and 0.1 g of mint oil are mixed, then added to 5 L of an aqueous solution containing 1% aspartame and 0.01% sodium ethylparaben to form an oil-in-water emulsion. The resultant solution is distributed to 5 ml, 10 ml, 20 ml, or 50 ml bottles for oral administration depending on the needs of patients.

EXAMPLE 17

Preparation of Oral Oily Liquid of Self-emulsifying Butylphthalide

The formulation is prepared substantially in the same way as in Example 12, except that an antiseptic agent such as ethylparaben and aspartame (before being added, aspartame can be firstly dispersed by a small amount of alcohol) is added when preparing the oily liquid. Colorless clear oily liquid is obtained by mixing, then directly distributed into graduated bottles for oral administration. Upon use, a measured use of the oral liquid is taken and added into water to form an oil-in-water emulsion for administration. Alternatively it is possible for the emulsion to be directly administered, which spontaneously forms an oil-in-water emulsion when getting contact with the body fluid.

EXAMPLE 18

A Pharmacokinetic Experiment in Rats after Oral Administration of Soft Capsules of Self-emulsification Butylphthalide The soft capsules of self-emulsifying butylphthalide prepared in Example 1 are used in the pharmacokinetic experiment after oral administration in rats. The results are compared to those obtained from commercially available soft capsules (the content is the mixture of 100 mg of butylphthalide and 300 mg of vegetable oil. Manufactured by NBP company of SHIJIAZHUANG PHARM. GROUP). They are shown in Table 3.

TABLE 3

The concentration of butylphthalide in blood plasma of rats at various time points after gavage

| Sampling point (hr) | Blood concentration of butylphthalide (μg/ml) | |
|---|---|---|
| | Normal soft capsules | Self-emulsifying soft capsules |
| 0.08 | 5.32 | 13.62 |
| 0.17 | 6.79 | 16.17 |
| 0.5 | 8.06 | 12.25 |
| 0.8 | 7.02 | 9.3 |
| 1 | 10.15 | 9.32 |
| 2 | 4.22 | 6.61 |
| 3 | 4.31 | 7.43 |
| 5 | 4.04 | 4.36 |
| 7 | 9.5 | 2.54 |
| 9 | 5.16 | 1.92 |
| 12 | 2.5 | 1.36 |

From Table 3, it can be seen that the present self-emulsifying drug delivery system achieves the peak concentration of the drug more rapidly than normal oily content. Their $t_{max}$ is 0.1 and 1.0 h, respectively. Additionally, the peak concentration achieved by the present soft capsules is higher than that achieved by normal soft capsules. Fewer individual variations are observed with the present soft capsules.

It is believed from the description above that after entering gastrointestinal tract, SEDDS is firstly self-emulsified into emulsion droplets, and subsequently rapidly dispersed throughout the gastrointestinal tract, thereby reducing the absorption difference in individuals due to the poor dispersion of the oil droplets, and reducing the irritation caused by the direct contact of the drug with the mucous membrane of the gastrointestinal tract. Additionally, the organization of the emulsion microdroplets may be changed or destroyed in the gastrointestinal tract. Above all, promising clinical values are demonstrated by the application of self-emulsifying drug delivery system to the lipid soluble and less water soluble oily drug—butylphthalide.

What to be claimed is:

1. A butylphthalide self-emulsifying drug delivery system, characterized in that it comprises by weight 25.3% to 65% of butylphthalide, 10% to 65% of an emulsifying agent, and 0% to 64.7% of an excipient, based on the weight of the self-emulsifying drug delivery system of butylphthalide.

2. The butylphthalide self-emulsifying drug delivery system according to claim 1, comprising by weight 25.3% to 50% of butylphthalide, 15% to 60% of an emulsifying agent, and 5% to 59.7% of an excipient, based on the weight of the self-emulsifying drug delivery system of butylphthalide.

3. The self-emulsifying drug delivery system of butylphthalide according to claim 1 or 2, wherein the butylphthalide is selected from the group consisting of its racemic, levo-rotary and dextro-rotary isoforms.

4. The butylphthalide self-emulsifying drug delivery system according to claim 1 or 2, wherein the emulsifying agent is chosen from any one of the group consisting of: liquid or solid ethoxy polyoxyethylene glyceride, polyoxyethylene oleate, liquid lecithin, polyoxyethylene castor oil, coconut oil, polyethyleneglycol glyceride, almond oil oleate polyethyleneglycol glycerin ester, polyoxyethylene glycerin trioleate, polyoxyethylene sorbitan oleate, and polyethyleneglycol-8 glycerin caprylate/caprate, or the mixture of any two or more thereof.

5. The butylphthalide self-emulsifying drug delivery system according to claim 1 or 2, further comprising water, a solubilizing agent and a flavoring.

6. The butylphthalide self-emulsifying drug delivery system according to claim 1 or 2, wherein the excipient is selected from edible vegetable oils.

7. The butylphthalide self-emulsifying drug delivery system according to claim 6, wherein the vegetable oils are selected from any one of the group consisting of sesame oil, corn oil, peanut oil, soybean oil, almond oil, peach kernel oil, cotton seed oil, sunflower seed oil, and olive oil, or the mixture of any two or more thereof.

8. The butylphthalide self-emulsifying drug delivery system according to claim 4, wherein the emulsifying agent is the mixture of polyoxyethylene castor oil and polyethyleneglycol-8 glycerin caprylate/caprate at the ratio of 1:0.5 to 1.5 by weight.

9. The butylphthalide self-emulsifying drug delivery system according to claim 1, wherein the self-emulsifying drug delivery system of butylphthalide is in the dosage form of oral liquid, soft capsule, hard capsule, delayed release capsule, oral solid powder or granule, tablet, or delayed release tablet.

10. A process for the preparation of the butylphthalide self-emulsifying drug delivery system of according to claim 1, comprising completely melting and mixing the emulsifying agent in a water bath at 20 to 60° C., then adding butylphthalide with agitation and mixing, and adding the excipient, to prepare a dosage form according to the butylphthalide self-emulsifying drug delivery system.

11. The butylphthalide self-emulsifying drug delivery system according to claim 1, wherein the weight ratio of butylphthalide to emulsifying agent is greater than or equal to 2:1.

12. The butylphthalide self-emulsifying drug delivery system according to claim 1, wherein the weight ratio of butylphthalide to emulsifying agent is 2:1.

13. A butylphthalide self-emulsifying drug delivery system, characterized in that it comprises by weight 20% to 65% of butylphthalide, 10% to 65% of an emulsifying agent, and 0% to 70% of an excipient, based on the weight of the self-emulsifying drug delivery system of butylphthalide, wherein the weight ratio of butylphthalide to emulsifying agent is greater than or equal to 2:1.

14. The butylphthalide self-emulsifying drug delivery system according to claim 13, wherein the weight ratio of butylphthalide to emulsifying agent is 2:1.

* * * * *